United States Patent
Ameling et al.

(10) Patent No.: US 7,597,848 B1
(45) Date of Patent: Oct. 6, 2009

(54) DEVICE FOR TRANSPORTING AND HOLDING MICROTITER PLATES

(75) Inventors: Richard Ameling, Aalen (DE); Thilo Enderle, Rheinfelden (DE); Christof Fattinger, Blauen (CH); Martin Gluch, Jena (DE); Hansjoerg Tschirky, Ettingen (CH)

(73) Assignees: Carl Zeiss Jena GmbH, Jena (DE); F. Hoffmann-LaRoche AG, Basil (CH)

( * ) Notice: Subject to any disclaimer, the term of this patent is extended or adjusted under 35 U.S.C. 154(b) by 0 days.

(21) Appl. No.: 09/509,921

(22) PCT Filed: Jul. 30, 1999

(86) PCT No.: PCT/EP99/05542

§ 371 (c)(1),
(2), (4) Date: Jun. 26, 2000

(87) PCT Pub. No.: WO00/08473

PCT Pub. Date: Feb. 17, 2000

(30) Foreign Application Priority Data

Aug. 4, 1998 (DE) ................... 198 35 071

(51) Int. Cl.
*G01N 21/00* (2006.01)
(52) U.S. Cl. .............. 422/65; 422/63; 422/67; 422/99; 422/100; 436/43; 436/180
(58) Field of Classification Search ........... 422/99–100, 422/63–67; 436/43, 180
See application file for complete search history.

(56) References Cited

U.S. PATENT DOCUMENTS 5,928,952 A * 7/1999 Hutchins et al. ............. 436/50

FOREIGN PATENT DOCUMENTS

| EP | 0 809 112 | 11/1997 |
|----|-----------|---------|
| EP | 0 915 341 | 5/1999 |
| WO | WO 97/22882 | 6/1997 |
| WO | WO 98/26295 | 6/1998 |
| WO | WO 98/52047 | 11/1998 |

OTHER PUBLICATIONS

XP-002122104 / Spektrum der Wissenschaften, Spezial 6: Pharmaforschung, 1997 (pp. 28-35) "Neue Wirkstoffe durch kombinatorische Chemie" M.J. Plunkett, et al.

* cited by examiner

*Primary Examiner*—Jill Warden
*Assistant Examiner*—Jyoti Nagpaul
(74) *Attorney, Agent, or Firm*—Reed Smtih LLP

(57) ABSTRACT

A transport system for transporting and handling microtiter plates, for use in high throughput screening, diagnosis and/or combinatorial chemistry, comprising modules with devices for preparing specimens and/or introducing specimens, and/or for optical readout and/or for plate storage and/or devices for further processing steps or readout steps. The system includes an inter-modular transport system for transporting the microtiter plates between the different devices and at least one central transport system for asynchronous plate transfer between individual modules via input and output buffers.

4 Claims, 3 Drawing Sheets

DEVICE FOR TRANSPORTING AND HOLDING MICROTITER PLATES

BACKGROUND OF THE INVENTION a) Field of the Invention

The invention relates to a device for transporting and for handling microtiter plates, wherein by microtiter plates is meant standardized carriers for specimens to be examined and/or processed for development of pharmaceutic agents in medical diagnoses or the like.

b) Description of the Related Art

The prior art in this field is substantially set forth in the following publications:
1. "Accelerating Drug Discovery Process with Automation and Robotics in High Throughput Screening", Ed.: John P. Delvin, 1997 Marcel Decker Inc., ISBN 0-8247-0067-8;
2. Examples in "Laboratory Automation News", Ed.: Robin A. Felder, Health Sciences Center Charlottesville, Va. 22908;
3. "Microplate Standardization Report 3", Journal of Biomolecular Screening, Vol. 1, No. 4, 1996;
4. "Spektrum der Wissenschaft Spezial Nr. 6", Pharmaforschung 1997, Spektrum der Wissenschaft Verlagsgesellschaft mbH, Heidelberg, ISSN 0943-7096 . . . ;
5. "Industrieroboter [Industrial Robots]", Kreuzer/Lugtenburg/MeiBner/Trukenbrodt 1994, Springer Verlag ISBN 3-540-54630-8.

The following abbreviations will be used hereinafter:
HTS high throughput screening
MTP microtiter plate
SPS stored program control.

The analysis of a large number of specimens is a recurring task in the development of pharmaceutic substances as well as in medical diagnoses.

The development of a new pharmaceutic substance is a process extending over a number of years and incurring high costs. In this process, a suitable pharmacogenic substance is sought as target structure (target) (see prior art reference 4). By means of a suitable biochemical determining reaction (assay), reactions between targets and suitable bonding partners can be detected quantitatively.

There currently exist in the pharmaceutics industry libraries of active agents with from 300,000 to 1,000,000 different pure substances. With each new target, bonding partners or ligands must be identified from these substances with a suitable assay. This process is known as high throughput screening (HTS). A screening of this kind results in a small quantity of substances (typically 0.5% to 1% of the total number) showing a positive reaction in the assay. These cardinal structures represent the basis for the continued development of a medication.

In medical diagnoses, similar problems result when infections, diseases, genetic disposition and the like are to be determined through analysis of a number of individual specimens (in this case mostly blood specimens, urine specimens, and so on) based on standardized determining reactions. An example of this would be screening in blood banks of donor blood for infections and routine examinations in risk groups for infections or other symptoms of illness.

Another area of application in the field of biochemistry is combinatorial chemistry. In this case, several hundred different individual substances are generated simultaneously by parallel synthesis and must be processed and characterized subsequently by suitable techniques.

A specimen carrier standard has been developed for parallel processing of large quantities of specimens: microtiter plates (MTP) with standardized dimensions and 96-well, 384-well and 1536-well grids (see prior art reference 3). This arrangement enables parallel processing of many individual specimens. Analysis for such MTPs is carried out by automatic running of assay protocols. A protocol of this kind comprises a fixed quantity of processing steps, including, for example, dissolving and mixing of substances, incubating for a fixed period of time and determining measurement values by means of a suitable analyzing device. For this purpose, there are automated specimen processing devices (see prior art reference 2) for dissolving, pipetting, mixing, incubating, and measuring.

Typical HTS systems are laboratory devices which are linked together by a central handling system. Such a handling system essentially comprises a robot with grippers for MTP which transports the plates between individual stations either in a circular movement (revolving-sliding arm) or straight-line movement.

The running of individual work steps is regulated by software control (scheduler) which optimizes the flow of process steps with respect to any existing boundary conditions (e.g., plate may only be transferred to a free position; fixed time intervals must be maintained between successive process steps, etc.).

The performance or efficiency of such handling systems is limited because in most cases the robot arm is not located in the position in which the next operation is to be carried out. The time required for arriving at that position depends on the last operation carried out and is therefore not always the same.

A robot arm requires three movements to advance two plates by one position. The above-mentioned limitation must be taken into account by the software controlling the total system.

In order to link the process steps in a linear manner, it is necessary to adhere to the boundary condition of maintaining fixed time intervals between two processing steps for all operations.

In rotary cycles (revolving-sliding arm), the number and size of the components taking part in the process are limited, but paths are short. On the other hand, when moving on a straight line, the idle times in which the arm moves to the next position become increasingly longer as the length increases.

The control of a system of this kind is coordinated by the scheduler, that is, a program which calculates the flow of control commands with respect to time in such a way that every MTP undergoes the same treatment (process steps and process duration). There are two types of scheduler:

Static schedulers are those in which the flow of control commands with respect to time is calculated before the start of the process and is not updated.

Dynamic schedulers are those in which the flow of control commands with respect to time is calculated before the start of the process and continuously recalculated when there are deviations.

Dynamic schedulers can respond to changes resulting from slight disturbances or variations in the process, but at the cost of identical treatment of all plates. Both types of schedulers must carry out very complex optimizing resulting from the above-mentioned boundary conditions of the transport systems as currently used in HTS.

OBJECT AND SUMMARY OF THE INVENTION

It is the primary object of the invention to provide a transport system of the type mentioned in the beginning which overcomes the limitations described above.

According to the invention, the linear process flow is divided into partial steps which are carried out in autonomous processing units (modules), each having its own transport system.

All of the processing steps of a process requiring a fixed time relationship with one another, such as strict adherence to an incubation time, are combined in one module of this kind.

Transport between processing stations within a module is carried out synchronously: the sequence of operations depending on the respective process flow is freely definable. Every module has a buffer for incoming and outgoing plates. All modules have a common standardized interface.

Transport between the modules is carried out asynchronously with a separate transport system between the output buffer and input buffer of successive modules. The sequence of plate transport is freely definable. The control of a module is carried out via a local control unit.

The individual module controls are connected with one another via a standardized network (Ethernet, field bus or future developments) with an appropriate protocol (TCP/IP, CAN or future developments).

A master computer takes control over the entire system (client server architecture).

The transport system between the modules can be realized by:
 a linear transport system with grippers;
 a revolving-sliding arm with grippers and corresponding arrangement of modules (see prior art reference 5);
 a conveyor belt with stoppers and in/out locks for the plates at the modules.

The transport system within the modules can be realized by a conveyor belt with transfer systems to the individual components on the module. The following possibilities are available for transfer:
 by means of grippers as "pick and place" operations;
 by means of stoppers on the belt in combination with input slides and output slides between the transport system and the individual components;
 rotary table with 2 receptacles for MTPs between which the plates are moved;
 articulated-arm robot (see prior art reference 5) within whose reach the individual components are located.

The controlling of the module can be realized by:
 stored program control (SPS), e.g., Siemens S5;
 industrial PC with plug-in locations;
 microcontroller with peripheral modules (PLC=programmable logic controller).

The control of the entire system can be realized, for example, by the following:
 stored program control (SPS), e.g., Siemens S5; or
 industrial PC with plug-in locations.

BRIEF DESCRIPTION OF THE DRAWINGS

In the drawiwngs.

DESCRIPTION OF THE PREFERRED EMBODIMENTS

In one embodiment example, the control would be carried out by the arrangement of module controls and the master computer in a client server architecture. The control units are PCs which are linked with one another by Ethernet. The operating system used for realizing communications via Ethernet by means of TCP/IP is, e.g., Windows NT.

Figure 1:
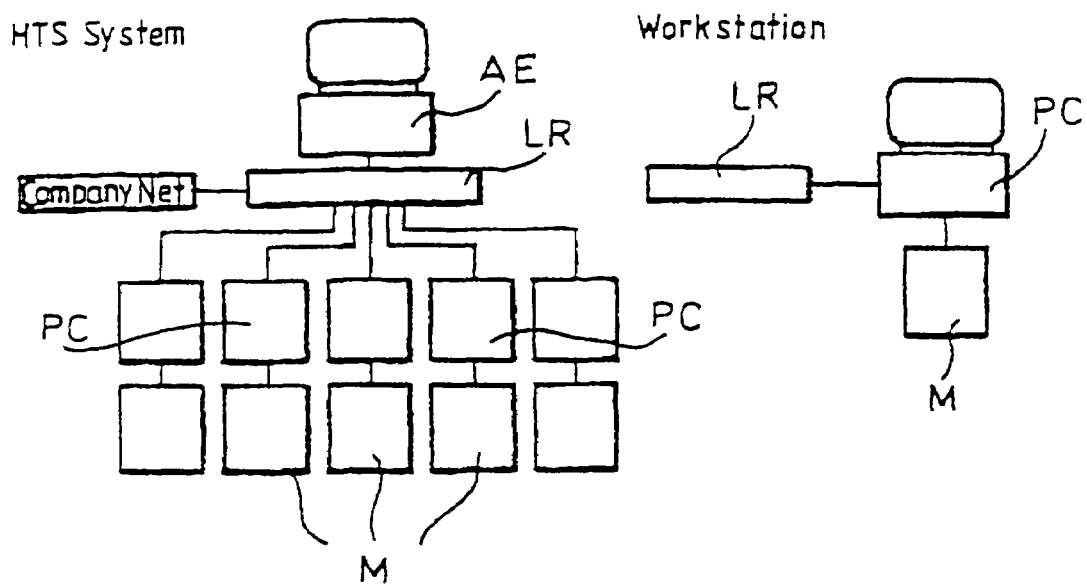
FIG. 1 shows communication via Ethernet by TCP/IP.

This is shown in FIG. 1. Every module M has a local computer PC and all local computers have the same interface and are connected with a master computer LR via module M. The different hardware within module M is controlled via the local computer PC, and the master computer LR has access via the uniform interfaces to the hardware operated in module M and controls the latter via a control unit AE.

The above-mentioned construction has the following advantages: the process steps which are critical with respect to time are comprised in module M which receives and transfers microtiter plates via buffers. Because of the buffers, not all of the process steps need to be synchronized in the control of plate flow but, rather, only those processes occurring within a module M.

Modules M are autonomous functional units that can carry out partial steps of a process. They can be operated alone without the entire system by a suitable control. In sole operation, the transfer of microtiter plates is carried out either via the buffer locations or with additional plate storages (stackers) which can receive and transfer a plurality of microtiter plates.

The modules M are less complex than the entire system. This facilitates maintenance and integration of new hardware as well as the testing of new processes. When module M functions, integration into the entire system based on the standardized interface is ensured.

The entire system is scalable. Modules M can be added or removed. A belt system serving as central transport means can be lengthened. Efficiency can be increased by the parallel connection of modules M.

Figure 2:
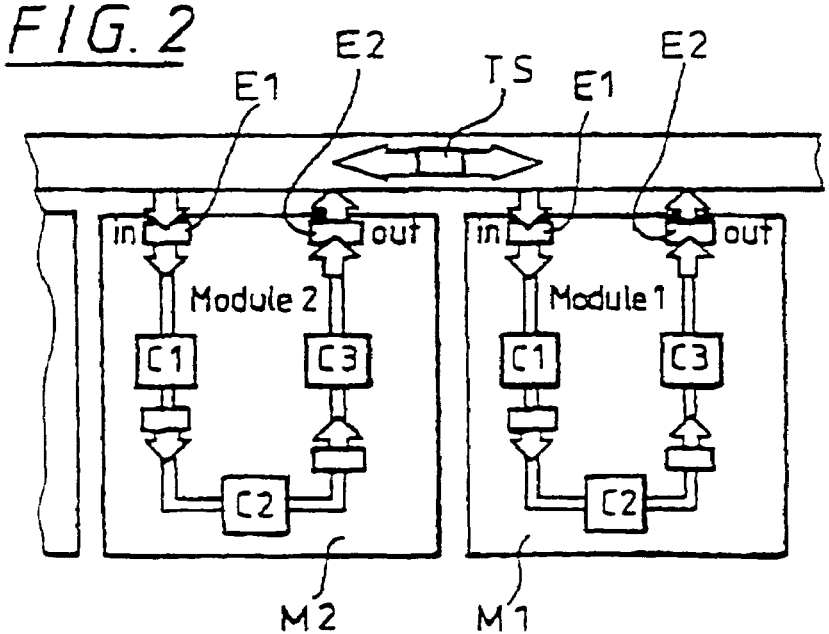
FIG. 2 shows the principle of synchronous/asynchronous plate transport.

FIG. 2 shows the principle of synchronous/asynchronous microtiter plate transport.

The drawing shows two modules M1, M2, each with a plurality of laboratory devices C1, C2, C3, e.g., pipetting devices, readers and incubators required for handling of specimens in microtiter plates.

Modules M1, M2 have contact with a central transport system TS (e.g., a conveyor belt) at the transfer point E1 for advancing the microtiter plates into one of the modules M1 or M2 and at the transfer point E2 for conveying microtiter plates out of modules M1, M2, wherein transport system TS takes over the transport between modules M1, M2, but also between the input storage units for the microtiter plates that are to be read out and end storage units for microtiter plates that have been read out.

Transfer to units E1, E2 can be carried out, for example, via sliding units by raising and lowering the microtiter plates or via grippers.

Figure 3:
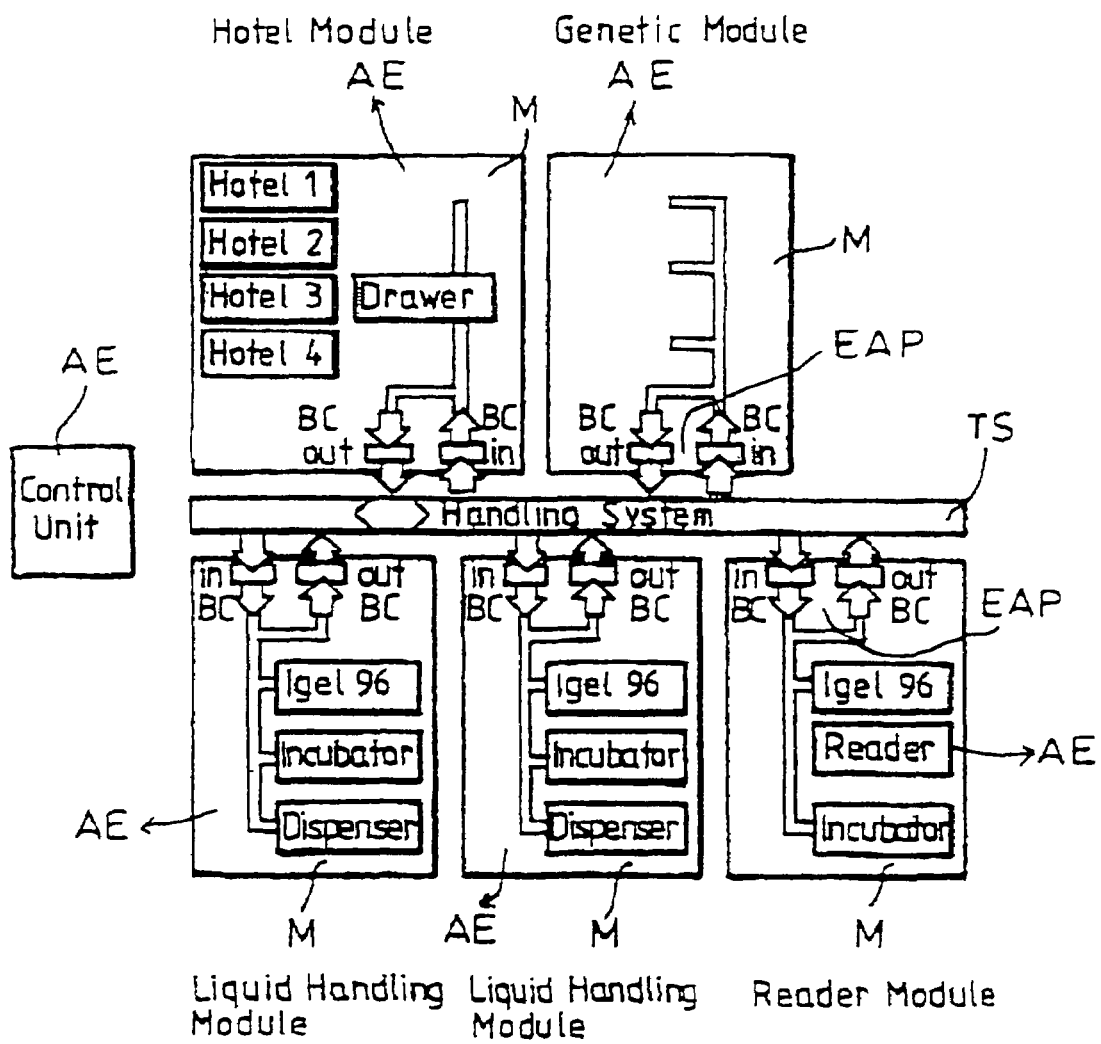
FIG. 3 shows the total system according to the invention.

FIG. 3 shows the entire system according to the invention comprising the central transport system TS and input and output buffers EAP for transferring microtiter plates to/from the transport system TS.

Figure 4:
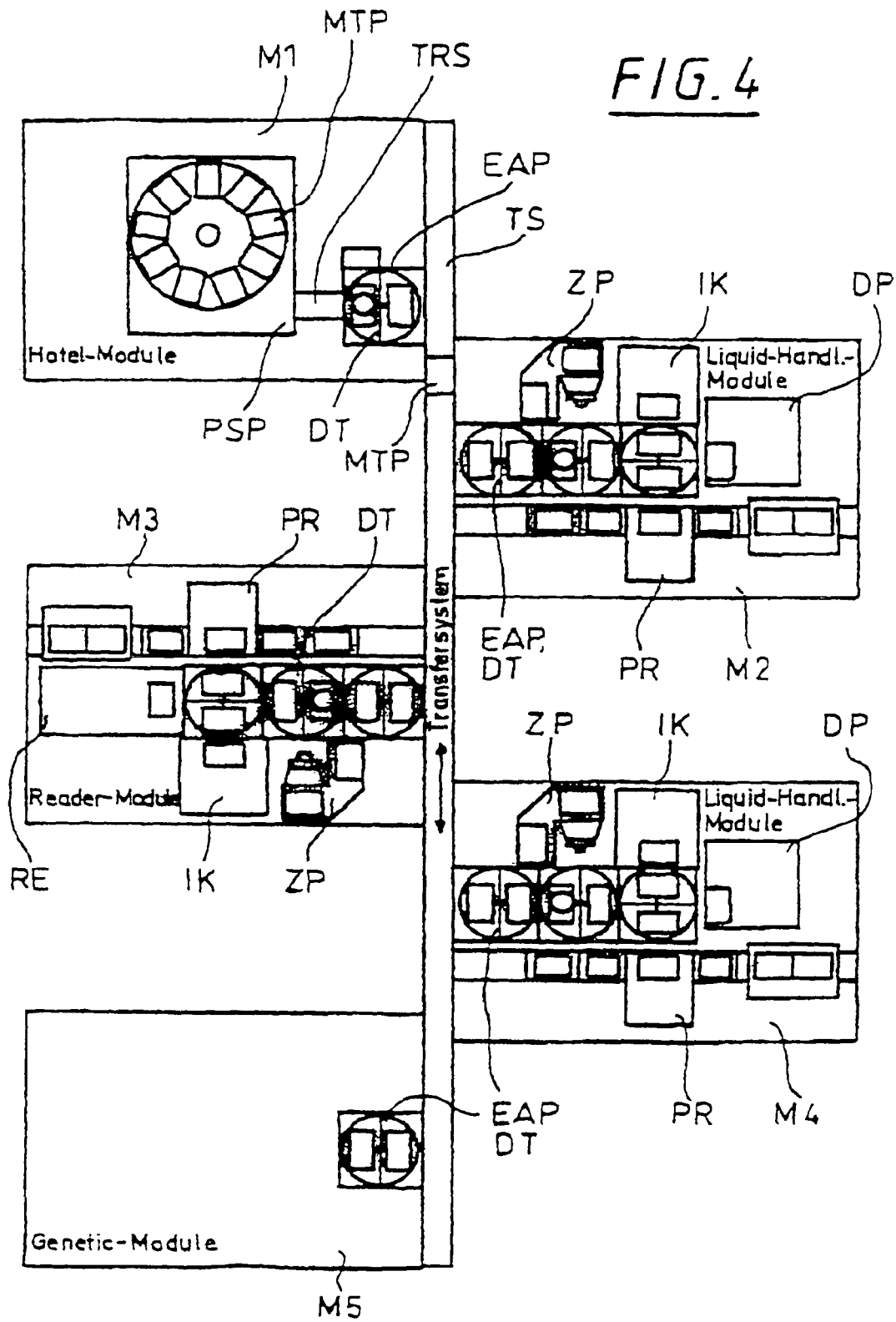
FIG. 4 shows the transfer of microplates to/from the transport system.

A more detailed view is shown in FIG. 4. In FIG. 4, a revolving table DT assumes the function of input and output buffer EAP with its two plate positions. A microtiter plate MTP is lifted from the central transport system TS and conveyed to the revolving table DT via a stopping-sliding device (not shown). The latter revolves and, in the diametrically opposite position of the revolving table DT, the microtiter plat MTP is taken over by other revolving tables DT by means of which the feed to module units M1, M2, M3, M3 or provided incubators IK, dispensers DP and pipetting robots PR is also carried out.

On the respective remote side of the revolving table DT, a microtiter plate MTP which has already been processed can be loaded simultaneously, and during rotating of the revolving table DT this microtiter plate MTP can then be transported in the direction of the module output or a stacker ZP for stacking microtiter plates MTP.

A sensor, for example, which detects whether or not the respective side of the revolving table DT is unoccupied can ensure that no collisions occur, so that a microtiter plate MTP can be loaded for return transport.

Another possible variant would be a clocked operation, so that the revolving table DT is always inserting one microtiter plate MTP and guiding out another microtiter plate MTP.

The reader RE for optical readout of the microtiter plates MTP shown in FIG. 4 in module M3 by way of example can also be a component part of module M.

Readout by means of reader RE can be carried out one or more times by transmitted light or incident light, wherein absorption, fluorescence, luminescence, scintillation or other occurring effects can be determined for the individual specimens.

The detection of fluorescence, for instance, is described in prior art reference 1, pages 357 to 356.

Additional intermediate storages ZP can be provided for the microtiter plates MTP in modules M1 to M5.

For example, preparation of specimens can also be carried out via module M2 and the readout via an optical reader RE can be carried out in module M3.

A plate storage PSP communicating with the transport system TS via a transfer system TRS and a revolving table DT is provided, by way of example, in module M1. Module 5 can be outfitted with additional devices and connected with the transport system TS via a revolving table DT.

While the foregoing description and drawings represent the present invention, it will be obvious to those skilled in the art that various changes may be made therein without departing from the true spirit and scope of the present invention.

What is claimed is:

1. A transport system for transporting and handling microtiter plates, for use in high throughput screening, diagnosis and/or combinatorial chemistry, the transport system comprising:
    modules, each with a device for at least one or more of the following: preparing specimens, introducing specimens, optical readout, plate storage, and further processing steps or readout steps; and
    at least one central transport system, which is separate from the modules and asynchronously transfers the plates between individual modules;
    wherein each of the modules includes a respective internal transport system which transports plates between the central transport system and the respective device of each module, each internal transport system including at least one revolving table having two plate locations for holding two respective plates;
    wherein the at least one revolving table of each module functions as an input and output buffer to transfer the plates to and from the at least one central transport system.

2. The transport system according to claim 1;
    wherein at least one of the modules is connected with a local computer with externally standardized interface and the transport and/or processing and/or loading and/or optical readout are/is controlled by a master computer via these interfaces.

3. The transport system according to claim 1, including a sensor which detects whether or not the respective side of the revolving table is unoccupied to ensure that no collisions occur so that a microtiter plate can be loaded for return transport.

4. The transport system according to claim 1, including means for providing a clocked operation so that a revolving table is always inserting one microtiter plate and guiding out another microtiter plate.

* * * * *

UNITED STATES PATENT AND TRADEMARK OFFICE
CERTIFICATE OF CORRECTION

PATENT NO. : 7,597,848 B1  Page 1 of 1
APPLICATION NO. : 09/509921
DATED : October 6, 2009
INVENTOR(S) : Ameling et al.

It is certified that error appears in the above-identified patent and that said Letters Patent is hereby corrected as shown below:

Title Page, Item (54) and Column 1, "HOLDING" should read "HANDLING".

"DEVICE FOR TRANSPORTING AND HANDLING MICROTITER PLATES"

Signed and Sealed this

Twenty-second Day of December, 2009

David J. Kappos
*Director of the United States Patent and Trademark Office*